United States Patent [19]
McGill et al.

[11] 4,066,423
[45] Jan. 3, 1978

[54] ADSORPTION-ABSORPTION VAPOR RECOVERY SYSTEM

[75] Inventors: James C. McGill; William N. Scott, both of Tulsa, Okla.

[73] Assignee: HT Management Company, Tulsa, Okla.

[21] Appl. No.: 726,822

[22] Filed: Sept. 27, 1976

[51] Int. Cl.² .............................................. B01D 53/04
[52] U.S. Cl. ............................................ 55/48; 55/58; 55/88
[58] Field of Search .................. 55/58, 68, 74, 75, 88, 55/89, 179, 387, 48; 220/85 VR, 85 VS

[56] References Cited
U.S. PATENT DOCUMENTS

| | | | |
|---|---|---|---|
| 3,648,436 | 3/1972 | Schonewald et al. | 55/88 |
| 3,714,790 | 2/1973 | Battey | 55/88 X |
| 3,770,622 | 11/1973 | Freireich et al. | 55/68 X |
| 3,771,317 | 11/1973 | Nichols | 55/88 X |
| 3,867,111 | 2/1975 | Knowles | 55/58 X |
| 3,947,258 | 3/1976 | Decker | 55/88 |
| 3,972,201 | 8/1976 | Datis | 55/58 X |

Primary Examiner—Thomas G. Wyse
Assistant Examiner—Robert H. Spitzer
Attorney, Agent, or Firm—Head, Johnson & Chafin

[57] ABSTRACT

A process for the recovery of light mixed hydrocarbon vapors from an air-hydrocarbon mixture expelled as a result of storage breathing or loading of a vented hydrocarbon vessel. The hydrocarbon vapor components are adsorbed from the mixture, thus permitting venting of the substantially hydrocarbon free air safely to the atmosphere without pollution. The adsorbed hydrocarbons are removed by subjecting the adsorbent bed to a lower pressure, and the hydrocarbon components in the resulting desorption stream are substantially adsorbed for recovery, and the remaining gases from the absorption vessel are passed through a second adsorption bed to substantially remove any hydrocarbons therein.

5 Claims, 2 Drawing Figures

ADSORPTION-ABSORPTION VAPOR RECOVERY SYSTEM

BACKGROUND OF THE INVENTION

The present invention relates to a process for the economical recovery of light mixed hydrocarbon components from the air-hydrocarbon vapor mixture which arises as a result of the vapor-liquid equilibrium established in a partially filled liquid hydrocarbon vessel. "Breathing" of the vessel or loading or refilling of same results in expulsion of an air-hydrocarbon vapor mixture to the atmosphere, polluting the environment, and creating a potential fire hazard. Common loading facilities involving crude oil storage tanks, truck and marine tankers, underground service station tanks, and numerous other industrial operations all have potential for such pollution and fire hazard. A means of controlling said pollution of the atmosphere thus becomes desirable and even required in some parts of the country where gasoline vapor emissions from service stations combined with high concentrations of photochemical oxidants in the atmosphere create smog problems. The economics of the losses resulting from the escaped hydrocarbons indicate need for a system whereby said hydrocarbon may be recovered for further use.

Various means have been devised for coping with hydrocarbon laden air, such as the vapor recovery and disposal system disclosed in U.S. Pat. No. 3,897,193. This particular process utilizes solid adsorbent beds for removal of the hydrocarbons from the air-hydrocarbon mixture, desorption of the hydrocarbon, and subsequent incineration thereof. Such a system requires a high investment; and in the event of the production of small quantities of hydrocarbon vapor, the heat derived from the incineration may not justify the expense of the equipment required. Furthermore, such an installation is impractical for a local service station which has little or no use for the heat produced. Numerous other methods, such as are disclosed in U.S. Pat. No. 3,455,089, U.S. Pat. No. 3,543,484, and U.S. Pat. No. 3,776,283, teach the adsorption of the hydrocarbon components from an air-hydrocarbon mixture, but fail to disclose, teach, or otherwise suggest a means for the economical recovery of said components.

The hydrocarbon recovery problems associated with all adsorbent systems lies in the varying vapor composition of the desorption stream during regeneration of the adsorbent bed. During the regeneration step, regardless of the method of regeneration chosen, the lightest hydrocarbons are desorbed first and followed by progressively heavier molecules until the heaviest components are extracted. The resulting continual change in regeneration vapor composition has heretofore hampered economical recovery of the hydrocarbon components.

Accordingly, it is an object of this invention to provide a method for the economical recovery of hydrocarbon components from an air-hydrocarbon mixture, thus achieving economies in the control of air pollution.

SUMMARY

The present invention teaches an efficient, economical method for the recovery of light mixed hydrocarbon vapors from an air-hydrocarbon mixture expelled from a vented tank as a result of storage breathing or during refilling of same with liquid hydrocarbon. As used herein, the term light hydrocarbons refers to hydrocarbons having a molecular weight less than 100. In accordance with the invention, the expelled air-hydrocarbon mixture is passed through a bed of solid adsorbent material, which is capable of selectively adsorbing the hydrocarbon components, resulting in an air stream which may be vented to the atmosphere substantially free of hydrocarbon contaminants, thus avoiding problems of pollution or fire hazard. During regeneration of the adsorbent bed, the pressure of the hydrocarbon laden bed is lowered to desorb hydrocarbon therefrom. The rich air-hydrocarbon mixture desorbed from the adsorbent bed is passed to an absorber where the hydrocarbon components of the mixture are substantially absorbed, and the remaining gaseous portion of the air-hydrocarbon mixture is passed through a second adsorbent bed for nearly complete removal of the remaining hydrocarbons prior to being vented to the atmosphere. It is of critical importance that the absorber be operated with a sufficiently high liquid to gas ratio to maintain a constant overhead vapor composition from the top of the absorber regardless of the inlet vapor composition to prevent premature saturation of the adsorption beds with the initially desorbed hydrocarbon components. As one adsorbent bed is operating in the regenerative mode, while the second bed is operating in the adsorption mode, continuous operation is possible.

DESCRIPTION OF THE PREFERRED EMBODIMENTS

Before describing the preferred embodiments of the present invention in detail for the better understanding and instruction of those who wish to apply the invention to their own particular needs, it is to be understood that the invention is not limited in application to the details of construction and arrangement of components as is illustrated in the accompanying drawings, as other and further modifications apart from those described or suggested herein, may be made in the spirit and scope of this invention. Also, it should be understood that the particular phraseology or terminology employed herein is for the purpose of illustration and instruction and not for the purpose of limitation.

Figure 1:
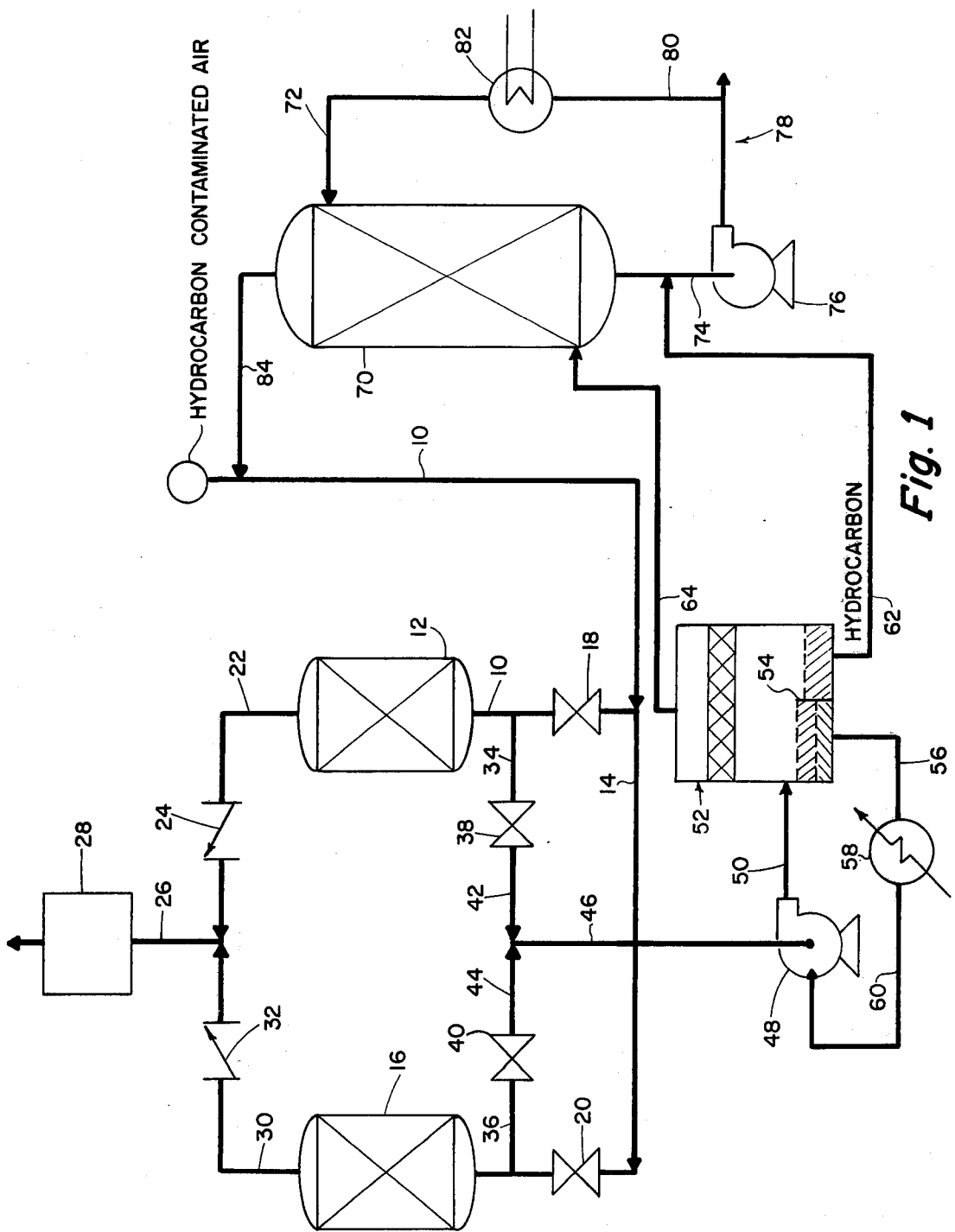
FIG. 1 is a flow sheet showing one of the preferred embodiments.

Referring now to FIG. 1, line 10 is connected from a source of light hydrocarbon contaminated air, such as that expelled from a gasoline storage tank, to the lower portion of adsorbent vessel 12. Line 14 is connected between line 10 and the lower portion of a second adsorbent vessel 16. Valve 18 is located in line 10 between adsorbent vessel 12 and the juncture of lines 10 and 14. Valve 20 is located in line 14. The adsorbent vessels are of standard design for holding solid adsorbent material, typically activated carbon, capable of selectively adsorbing the hydrocarbon components from an air-hydrocarbon mixture introduced therein. Lines 22 and 30 are connected from the upper portions of adsorbers 12 and 16 respectively to check valves 24 and 32 respectively. Check valves 24 and 32 are connected to line 26 which is connected to flame arrester 28. Material passing through flame arrester 28 is vented to the atmosphere. Line 34 is connected to line 10 between valve 18 and adsorber 12 and to valve 38. Line 36 is connected to line 14 between valve 20 and adsorber 16, and to valve 40. Valves 38 and 40 are connected to line 46 via lines 42 and 44 respectively. Line 46 is connected to the suction port of pump 48, and the pump discharge line 50 is connected between the pump 48 and the separator, generally indicated by reference character 52. Hydrocarbon contaminated air is introduced at a pressure slightly above atmospheric, and at the temperature of the mixture source, which is normally ambient, through line 10 to the lower portion of the adsorber bed 12 by opening valve 18 and closing valves 20 and 38. As the air-hydrocarbon mixture flows through the adsorbent packed in the vessel, substantially all of the hydrocarbon is adsorbed therefrom, and clean air is expelled from the top of the adsorber through line 22 and check valve 24. From check valve 24, the air passes through line 26, flame arrester 28, and therefrom to the atmosphere. As is apparent, check valve 32 prevents effluent air from adsorber 12 from entering the top of adsorbent bed 16. Prior to reaching the saturation point of the adsorbent material in adsorbent vessel 12, valves 18 and 40 are closed, and valve 20 is open to route the air-hydrocarbon mixture from line 10 through line 14 to adsorber 16 for use during the regeneration of the adsorbent in adsorber 12. Pump 48 is a liquid ring vacuum pump capable of producing a near vacuum in either adsorbent bed during regeneration. The use of a liquid ring pump is advocated to minimize risks of explosion. Valve 38 is opened, and the vacuum produced by pump 48 in the adsorbent vessel desorbs the hydrocarbon from the adsorbent to produce a rich air-hydrocarbon mixture comprised of approximately 85 to 90% hydrocarbon by volume. As this rich air-hydrocarbon mixture comes in direct contact with pumping liquid used by the pump, cooling of the air-hydrocarbon mixture will occur, and a portion of the heavier hydrocarbon components therein will condense. Effluent from pump 48 is admitted to separator 52 via line 50. Separator 52 is a vessel operated slightly above atmospheric pressure and designed to separate the vapor and liquid components of the pump effluent and to further separate the immiscible liquid used by the liquid ring pump from any recovered hydrocarbon liquid condensed by the inherent cooling action of said pump. The liquid components of the pump effluent are separated by means of a weir 54 located in the bottom portion of the separator 52 over which the lighter hydrocarbon liquid may flow. The heavier pumping liquid, typically water, trapped by the weir, is withdrawn from the bottom of the separator 52 by line 56 connected between the bottom of the separator and cooler 58. Antifreeze may also be used as pumping liquid in the liquid ring pump where freezing ambient temperatures are anticipated. Cooler 58 is an indirect heat exchanger and may employ any suitable cooling medium. Cooled pump liquid from cooler 58 is recycled for use in pump 48 through line 60 connected between cooler 58 and the pump 48. Recovered liquid hydrocarbon overflowing the weir 54 is withdrawn from separator 52 through line 62 connected between the lower portion of separator 52 and line 74 for use as a liquid adsorbent. The vapor phase of the pump effluent is withdrawn from separator 52 through line 64 connected between the upper portion of the separator and the bottom portion of absorber 70. Absorber 70 is a conventional absorber operated near ambient temperature and slightly above atmospheric pressure and may be of either tray or packed tower design. In absorber 70, the vapor from separator 52 comes in direct countercurrent contact with recovered hydrocarbon liquid introduced at the upper portion of the absorber via line 72 and the hydrocarbon components in the vapor are substantially absorbed. Recovered hydrocarbon liquid is withdrawn from the bottom of the absorber through line 74 connected between the bottom of the absorber and the suction port of pump 76. The recovered hydrocarbon liquid is discharged from the pump through line 78, and a portion of said recovered hydrocarbon liquid passes from line 78 through line 80 to cooler 82. The portion of the hydrocarbon liquid passing through cooler 82 is cooled and recycled to the top of absorber 70 via line 72 for use as absorbent. The remaining recovered hydrocarbon liquid is pumped via line 78 for use elsewhere. Vapor from the top of the absorber, comprising approximately 20 to 30% hydrocarbon by volume, passes by line 84 from the top of the absorber to line 10 for recycling through the adsorption bed 16. The absorber must be operated within a sufficiently high absorbent liquid to feed gas ratio to maintain a constant overhead vapor composition from the top of the absorber regardless of fluctuations in composition of the inlet feed gas. It has been discovered that a ratio of 40 moles of liquid absorbent per mole of feed gas is adequate for gasoline vapor recovery systems using gasoline at ambient temperature for the liquid absorbent. It is readily observed that this particular embodiment permits the continuous removal of hydrocarbon from hydrocarbon-contaminated air as a result of operating two adsorption beds in reciprocal modes. After the desired level of reactivation is attained in adsorption bed 12, said bed may again be placed in the adsorption mode, and adsorption bed 16 may be regenerated at that time.

Figure 2:
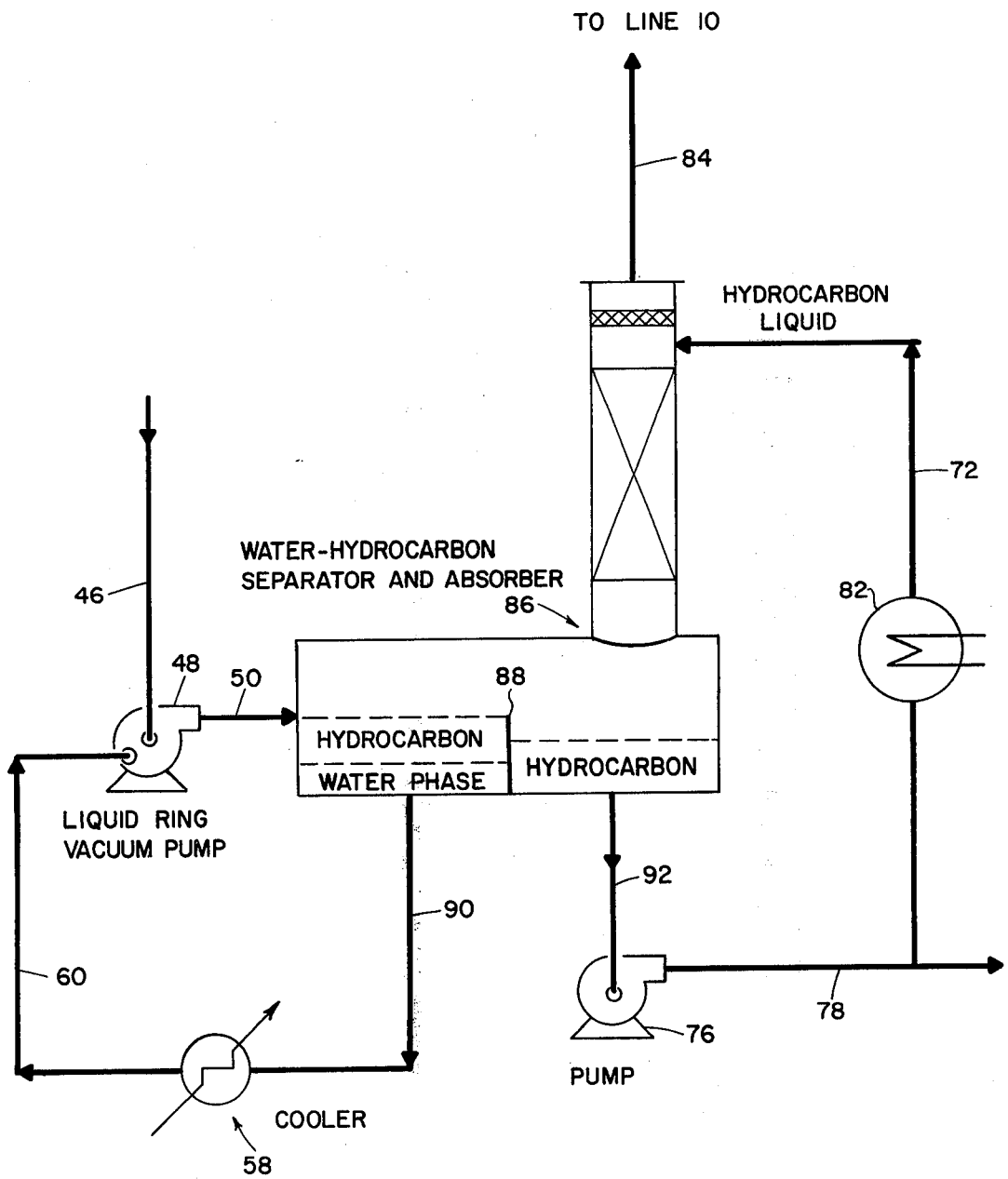
FIG. 2 is a flow sheet showing a modification of the process as same relates to FIG. 1.

A second embodiment of the invention may be more readily described with reference to FIG. 2 of the drawings. As shown therein, line 46 is the suction line from the adsorbers shown in FIG. 1 to liquid ring vacuum pump 48. The discharge from liquid ring vacuum pump 48 passes through line 50 to a water-hydrocarbon separator and absorber unit, generally indicated by reference character 86. As shown therein, the liquid phase of the pump effluent, comprised of recovered hydrocarbon liquid and water is separated by a weir 88 which permits the lighter hydrocarbon to overflow and the water retained by the weir is withdrawn from the separator portion of the apparatus through line 90 connected between the bottom of unit 86 and cooler 58. The cooled water from cooler 58 is recycled via line 60 to the liquid ring vacuum pump as mentioned above. The vapor phase of the pump effluent discharge enters the bottom of the absorber portion of unit 86, which may be of tray or packed tower design, where it comes in direct countercurrent contact with recovered hydrocarbon liquid introduced at the top thereof via line 72. After a substantial portion of the hydrocarbon components are absorbed from said vapor, the remaining vapor is withdrawn from the top of the absorber through line 84 to be recycled to the adsorption unit. Recovered hydrocarbon liquid from the vapor phase and the hydrocarbon used as absorbent, mixed with the liquid hydrocarbon overflowing weir 88, is withdrawn from the bottom of unit 86 through line 92 connected to the suction port of pump 76. Pump 76 discharges into line 78, and a portion of the recovered hydrocarbon liquid is withdrawn from line 78 by line 72 where it is cooled in exchanger 82 and returned to the top of the absorber for use as absorbent. The remainder of the recovered liquid hydrocarbon is pumped through line 78 for use elsewhere. Again, it is imperative that the L/V mole ratios maintained in the absorber portion be sufficiently high to achieve a constant overhead gas composition.

What is claimed is:

1. A process for recovering light hydrocarbon from an air-hydrocarbon mixture, comprising:

passing the air-hydrocarbon mixture through a solid adsorbent bed operated at slightly above atmospheric pressure, capable of selectively adsorbing hydrocarbon components from the mixture to leave substantially hydrocarbon free air;

venting the substantially hydrocarbon free air to the atmosphere;

lowering the pressure of the hydrocarbon laden solid adsorbent bed by vacuum pumping to desorb the air-hydrocarbon components therefrom and produce a rich air-hydrocarbon mixture;

cooling the rich air-hydrocarbon mixture to near ambient temperature;

absorbing substantially all of the hydrocarbon components from the rich air-hydrocarbon mixture with a liquid hydrocarbon absorbent in an absorber operating with a sufficiently high L/V ratio to produce a constant composition absorber overhead gas containing hydrocarbon and a recovered liquid hydrocarbon, mixed with said absorbent;

recycling the absorber overhead gas from the absorption step to a second solid adsorbent bed, capable of selectively adsorbing the hydrocarbon contained in said absorber overhead gas to leave a substantially hydrocarbon free recycle air;

venting the substantially free hydrocarbon recycle air to the atmosphere;

cooling a portion of the recovered liquid hydrocarbon; and recycling the cooled recovered hydrocarbon liquid for use as liquid hydrocarbon absorbent in the absorption step.

2. A process for recovering hydrocarbon from an air-hydrocarbon mixture, comprising:

passing the air-hydrocarbon mixture through a solid adsorbent bed at slightly above atmospheric pressure, which bed is capable of selectively adsorbing the hydrocarbon components from the mixture to leave substantially hydrocarbon free air;

venting the substantially hydrocarbon free air to the atmosphere;

subjecting the hydrocarbon laden solid adsorbent bed to a near vacuum with a liquid ring vacuum pump to desorb the hydrocarbon components therefrom and produce a rich air-hydrocarbon vapor mixture containing a liquid from the liquid ring vacuum pump and a recovered liquid hydrocarbon;

separating the liquid from the liquid ring vacuum pump and the recovered liquid hydrocarbon from the rich air-hydrocarbon vapor mixture;

absorbing substantially all of the hydrocarbon components from the rich air-hydrocarbon vapor mixture with recovered liquid hydrocarbon absorbent in an absorber operating with a sufficiently high L/V ratio to produce a constant composition absorber overhead gas and a recovered liquid hydrocarbon mixed with said absorbent;

recycling the absorber overhead gas from the absorption step to a second solid adsorbent bed, capable of selectively absorbing the hydrocarbon therein to leave a substantially free hydrocarbon recycle air;

venting the substantially free hydrocarbon recycle air to the atmosphere;

separating the liquid ring vacuum pump liquid from the recovered liquid hydrocarbon produced in the separation step;

cooling the liquid ring vacuum pump liquid; and recycling said liquid ring vacuum pump liquid for use in the liquid ring vacuum pump.

3. A process, as recited in claim 2, the further steps comprising:

cooling a portion of the recovered liquid hydrocarbon; and recycling the cooled recovered liquid hydrocarbon for use as absorbent in the absorption step.

4. A process, as recited in claim 3, wherein the liquid ring vacuum pump liquid is water.

5. A process, as recited in claim 3, wherein the liquid ring vacuum pump liquid is water mixed with an antifreeze material.

* * * * *